US010935518B2

(12) United States Patent
Wu et al.

(10) Patent No.: US 10,935,518 B2
(45) Date of Patent: Mar. 2, 2021

(54) DEVICES FOR AND METHODS OF PROCESSING BIOLOGICAL SAMPLES

(71) Applicants: Rongrong Wu, El Sobrante, CA (US); Guofu Wang, Wuhan (CN)

(72) Inventors: Rongrong Wu, El Sobrante, CA (US); Guofu Wang, Wuhan (CN)

( * ) Notice: Subject to any disclaimer, the term of this patent is extended or adjusted under 35 U.S.C. 154(b) by 208 days.

(21) Appl. No.: 15/996,466

(22) Filed: Jun. 2, 2018

(65) Prior Publication Data
US 2018/0348163 A1 Dec. 6, 2018

(30) Foreign Application Priority Data

Jun. 2, 2017 (CN) .......................... 201710407208.9

(51) Int. Cl.
*G01N 27/447* (2006.01)
*G01N 35/00* (2006.01)
*G01N 33/543* (2006.01)
*B01L 9/00* (2006.01)

(52) U.S. Cl.
CPC .......... *G01N 27/44739* (2013.01); *B01L 9/52* (2013.01); *G01N 27/44704* (2013.01); *G01N 27/44756* (2013.01); *G01N 33/54366* (2013.01); *G01N 35/0099* (2013.01); *G01N 2035/00306* (2013.01)

(58) Field of Classification Search
None
See application file for complete search history.

(56) References Cited

U.S. PATENT DOCUMENTS

| 5,350,502 A | * | 9/1994 | Brunk | .............. G01N 27/44717 204/606 |
| 7,033,477 B2 | * | 4/2006 | Alpenfels | ........ G01N 27/44704 204/466 |

OTHER PUBLICATIONS

E. J. Zapolski, et al. ("A system for automated DNA electrophoresis, molecular hybridization and electronic detection: I Electrophoresis and hybridization", Electrophoresis, 8(6): p. 255-261 (Year: 1987).*

* cited by examiner

*Primary Examiner* — J. Christopher Ball
(74) *Attorney, Agent, or Firm* — Feng Tian

(57) ABSTRACT

The present disclosure provides devices, systems and methods for automated processing of biological samples. This disclosure provides a gel-frame cassette for an automated bioprocessing device, comprising: a gel-frame comprising: a front face, a back face, a frame comprising: two vertical side bars, each comprising a gel-frame holding hole, a top bar connecting the two vertical side bars, a bottom bar connecting the two vertical side bars and a hollow chamber enclosed by the two vertical side bars, the top bar, and the bottom bar; a front panel in contact with the front face of the gel-frame, the front panel comprising an expanded upper portion, and a back panel in contact with the back face of the gel-frame, the back panel comprising a horizontal opening at the bottom of the back panel. This disclosure also provides an automated bioprocessing machine that processes the gel-frame cassette or the gel-frame.

12 Claims, 13 Drawing Sheets

DEVICES FOR AND METHODS OF PROCESSING BIOLOGICAL SAMPLES

CROSS REFERENCE

This present disclosure claims the benefits of Chinese Patent Application No. 201710407208.9 filed on Jun. 2, 2017, which is herein incorporated by reference in its entirety.

BACKGROUND

Historically, time-consuming and laborious manual manipulations are part of certain biological assays and lab procedures. Many of these manipulations would be amenable to and benefit from automation. For example, Western blot or protein immunoblot is an indispensable tool for modern biological scientific research. It is one of the comment experimental methodologies in molecular biology, biochemistry and immunogenetics. Its operational principle is to use specific antibodies to label cells or biological tissue samples after gel electrophoresis. Based on the label's position and thickness, information can be obtained for the expression of specific protein in the cells or tissues analyzed. Traditional Western blot methods rely on manual operations and suffer from low efficiency and non-automation for steps such as electrophoresis, membrane transfer, development and collection of signals.

SUMMARY

The following embodiments and aspects thereof are described and illustrated in conjunction with devices, systems and methods which are meant to be exemplary and illustrative, not limiting in scope.

The present disclosure provides automated devices, systems and methods to improve the efficiency of traditional bioprocessing. In some embodiments, bioprocess, such as, for example Western blot, is automated. In some embodiments, the electrophoresis, electroblotting, signal development and signal collection steps for Western blot are automated. Such automation may save a technician's time, reduce human error, improve consistency between different experiments, and reduce cost in the long run.

In one aspect, disclosed herein is a gel-frame cassette for an automated bioprocessing device, comprising: a gel-frame comprising: a front face, a back face, a frame comprising: two vertical side bars, each comprising a gel-frame holding hole, a top bar connecting the two vertical side bars, a bottom bar connecting the two vertical side bars and a hollow chamber enclosed by the two vertical side bars, the top bar, and the bottom bar; a front panel in contact with the front face of the gel-frame, the front panel comprising an expanded upper portion, and a back panel in contact with the back face of the gel-frame, the back panel comprising a horizontal opening at the bottom of the back panel.

In some embodiments, the gel-frame cassette further comprises a gel in the hollow chamber. In some embodiments, the gel forms covalent bonds with at least part of contacting surfaces on the two vertical side bars, the top bar, and the bottom bar. In some embodiments, an automated bioprocessing device processes the gel-frame cassette, the automated bioprocessing device comprising: an electrophoresis chamber comprising the gel-frame cassette; a plurality of processing chambers; and a robotic arm configured to transport the gel-frame cassette or the gel-frame to a chamber of the plurality of processing chambers. In some embodiments, the plurality of processing chambers comprises a separation chamber and an electroblotting chamber. In some embodiments, the plurality of processing chambers further comprises a blocking chamber, a washing chamber, and an antibody-incubation chamber. In some embodiments, the separation chamber comprises a wedge column configured to engage with the gel-frame cassette and remove the front panel and back panel from the gel-frame. In some embodiments, the electroblotting chamber comprises two holding pads, and a membrane-frame cassette in-between the two holding pads. In some embodiments, the antibody-incubation chamber comprises two expandable pouches, wherein the expandable pouches are configured to accommodate a membrane-frame cassette in-between the two expandable pouches.

In another aspect, disclosed herein is a center-hollow membrane-frame cassette for an automated bioprocessing device, comprising: a center-hollow structure comprising: a front panel, a back panel, a top panel comprising a top opening, and a bottom panel, together with the front panel and the back panel, comprising toothed openings on the bottom of the center-hollow structure, wherein the top opening, the front panel, and the back panel together define a gap.

In some embodiments, the front panel comprises a plurality of openings, and the back panel comprises another plurality of openings. In some embodiments, the center-hollow membrane-frame cassette further comprises a blotting membrane in the gap. In some embodiments, an automated bioprocessing device processes the center-hollow membrane-frame cassette, the automated bioprocess device comprising: a plurality of processing chambers; and a robotic arm configured to transport the center-hollow membrane-frame cassette to a chamber of the plurality of processing chambers. In some embodiments, the plurality of processing chambers comprises a blocking chamber, a washing chamber, and an antibody-incubation chamber. In some embodiments, the antibody-incubation chamber comprises two expandable pouches, wherein the expandable pouches are configured to accommodate the center-hollow membrane-frame cassette in-between the two expandable pouches. In some embodiments, the expandable pouch comprises a plurality of rope protrusions at the bottom of the expandable pouches, and wherein the plurality of rope protrusions is configured to agitate the blotting membrane through the toothed openings. In some embodiments, the washing chamber comprises a plurality of rod-shaped protrusions at the bottom of the washing chamber, and wherein the plurality of rod-shaped protrusions is configured to agitate the blotting membrane through the toothed openings.

In another aspect, disclosed herein is an automated bioprocessing device for Western blot, comprising: an electrophoresis chamber; a separation chamber; an electroblotting chamber; and a robotic arm configured to transport a gel-frame to any one of the electrophoresis chamber, the separation chamber, and the electroblotting chamber.

In some embodiments, the automated bioprocessing device for Western blot further comprises a blocking chamber, a washing chamber, and an antibody-incubation chamber. In some embodiments, the separation chamber comprises a wedge column.

In still another aspect, disclosed herein is a method for automated bioprocessing, comprising: providing a gel-frame cassette to an electrophoresis chamber of an automated bioprocessing device; conducting electrophoresis of a gel comprising protein samples; transferring the gel-frame cassette from the electrophoresis chamber to a separation chamber; and removing a front panel and a back panel from a gel frame of the gel-frame cassette in the separation chamber.

In some embodiments, the method further comprises, transferring the gel-frame from the separation chamber to an electroblotting chamber. In some embodiments, the method further comprises electroblotting the protein sample from the gel to a blotting membrane in the electroblotting chamber. In some embodiments, the method further comprises transferring the blotting membrane from the electroblotting chamber to a blocking chamber, an antibody incubation chamber, a washing chamber, a signal development chamber, or a signal collection chamber. In some embodiments, the method further comprises agitating the blotting membrane in the blocking chamber, the antibody incubation chamber, the washing chamber, the signal development chamber, or the signal collection chamber. In some embodiments, the robotic arm agitates the membrane in the antibody incubation chamber. In some embodiments, the method further comprises agitating the membrane by a plurality of protrusions in the blocking chamber, the antibody incubation chamber, or the washing chamber.

In one aspect, disclosed herein is a bioprocessing device comprising: a loading component for protein samples, an electrophoresis component for protein samples, an electroblotting component to transfer protein samples from a gel to a blotting membrane, an antibody-treatment component for the blotting membrane, a signal development component for the blotting membrane, and signal collection/output component.

In some embodiments, the loading component for protein samples is controlled by a processor, such as, for example, a computer processor. In some embodiments, the loading component handles multi-sample-loading. In some embodiments, the electrophoresis component comprises a power source, a gel-frame cassette, an electrophoresis chamber, and a separation chamber. In some embodiments, the membrane-frame cassette is in a rectangular shape. In some embodiments, the side bars on the left and right sides of the membrane-frame cassette protrude above the membrane-frame top bar, with the membrane-frame holding holes on the top part of the protruding side bars.

In some embodiments, the electroblotting chamber contains an electroblotting solution. In some embodiments, the electroblotting chamber allows the insertion of a gel-frame inside the chamber and in fluid contact with the electroblotting solution. In some embodiments, a membrane-frame cassette is pre-installed into the electroblotting chamber. In some embodiments, the membrane-frame cassette is confined at one side of the electroblotting chamber, moves vertically, but does not move horizontally. In some embodiments, there are holding pads inside the electroblotting chamber. In some embodiments, the holding pad is controlled by a computer processor. In some embodiments, the holding pad may use electromagnetic or mechanical force to hold subjects.

In some embodiments, the antibody-treatment component comprises: an antibody incubation chamber comprising pouches, a blocking chamber which is pre-loaded with antibody solution and accommodates the membrane-frame cassette, and a washing chamber. In some embodiments, the antibody incubation chamber comprises two pouches, each of which is attached to the bottom of the antibody incubation chamber. In some embodiments, there is a gap between the two pouches. In some embodiments, the gap accommodates the membrane-frame cassette. In some embodiments, the pouch is inflatable or expandable. In some embodiments, the inflated or expanded pouch force part of the solution or solvent stored in the chamber to move to the upper portion of the chamber.

In some embodiments, the signal development component for the blotting membrane and signal collection/output component are fluorescent substrate incubation chamber. In some embodiments, the device comprises multiple chambers for each component.

In some embodiments, the gel-frame cassette comprises a gel comb, a front panel, a gel-frame, and a back panel. In some embodiments, each of the two upper ends of the side arm of the gel-frame comprises a gel-frame holding hole. In some embodiments, the gel-frame holding hole engages with and is controlled by a robotic arm. In some embodiments, the gel-frame of the gel-frame cassette forms a composite with the gel through covalent chemical bonds. In some embodiments, the side of the gel-frame facing the gel comprises insert groove which comprises a geometry shape that facilitates the formation of the composite with the gel. In some embodiments, the front panel and the back panel of the gel-frame cassette is removable from the gel-frame.

In some embodiments, the front panel and the back panel are glass or plastics coated with a hydrophilic layer. In some embodiments, the front panel and the back panel are thin and pliable glass or thin plastics coated with a hydrophilic layer. In some embodiments, the front panel is rectangular. In some embodiments, the back panel comprises an expanded upper portion, together with the gel-frame and the front panel, forms an electrophoresis cathode chamber to hold electrophoretic solutions. In some embodiments, the back panel comprises a back panel bottom opening at the lower part of the back panel. In some embodiments, the back panel bottom opening is rectangular.

In some embodiments, the frame of the gel-frame forms covalent chemical bonds with the gel of the gel-frame.

In some embodiments, the left and right sides of the gel-frame cassette, enclosed by the front panel, back panel, and the sides of the gel-frame, form a W-shaped gap. In some embodiments, a wedge rod having a matching shape to the W-shaped gap is configured to insert into the W-shaped gap. In some embodiments, when the wedge rod with a matching shape to the W-shaped gap is inserted into the W-shaped gap, the front panel and the back panel are removed from the gel-frame cassette, leaving behind the gel-frame.

In some embodiments, the separation chamber comprises wedge column at the bottom of the separation chamber. In some embodiments, the wedge column is configured to remove the front panel and the back panel from the gel-frame cassette. In some embodiments, the wedge column comprises hollow chamber matching the side bar of the gel-frame for the separation of the gel-frame from the front panel and the back panel.

In some embodiments, the membrane-frame cassette comprises a membrane-frame. In some embodiments, the membrane-frame comprises a blotting membrane fixed inside the side bars of the membrane-frame. The fixation of the membrane into the membrane-frame is with mechanical force, via heating, by polymerization, or chemical methods. The blotting membrane is nitrocellulose membrane or polyvinylidene difluoride (PVDF) membrane, each of which binds proteins.

In some embodiments, a center-hollow membrane-frame cassette comprises a center-hollow structure, which accommodates the blotting membrane inside the center-hollow structure. In some embodiments, there are multiple openings on the front panel and back panel of the center-hollow structure, thereby allowing solvent/solution to enter into and exit from the center-hollow structure. In some embodiments, there are openings on the top panel and bottom panel of the center-hollow structure, thereby allowing solvent/solution to enter into and exit from the center-hollow structure. In some embodiments, the blotting membrane is movable within the center-hollow structure. In some embodiments, there are bumps the inner surface of center-hollow structure. In some embodiments, there are toothed openings on the bottom of the center-hollow membrane-frame cassette. In some embodiments, toothed protrusions on the bottom of a chamber are configured to protrude into the center-hollow membrane-frame cassette through the toothed opening, thereby agitating the blotting membrane.

In some embodiments, each of the blocking chamber, the antibody incubation chamber, and the washing chamber for the membrane-frame cassette comprises a flat bottom. In some embodiments, each of the blocking chamber, the antibody incubation chamber, and the washing chamber for the center-hollow membrane-frame cassette comprises toothed protrusions configured to agitate the blotting membrane inside the center-hollow membrane-frame cassette. In some embodiments, the antibody incubation chamber comprises pouches attached to the bottom of the antibody incubation chamber. In some embodiments, the pouches are inflatable or expandable. In some embodiments, there is a blocking chamber or gap in-between the pouches. In some embodiments, the blocking chamber or gap accommodates the membrane-frame cassette or the center-hollow membrane-frame cassette.

Further areas of applicability of the present disclosure will become apparent from the detailed description provided hereinafter. It should be understood that the detailed description and specific examples, while indicating various embodiments, are intended for purposes of illustration only and are not intended to limit the scope of the disclosure.

BRIEF DESCRIPTION OF THE DRAWINGS

The object and features of the present disclosure can be more fully understood and better appreciated with reference to the attached drawings, which are schematic representations only and not necessarily drawn to scale, wherein.

DETAILED DESCRIPTION

Figure 1:
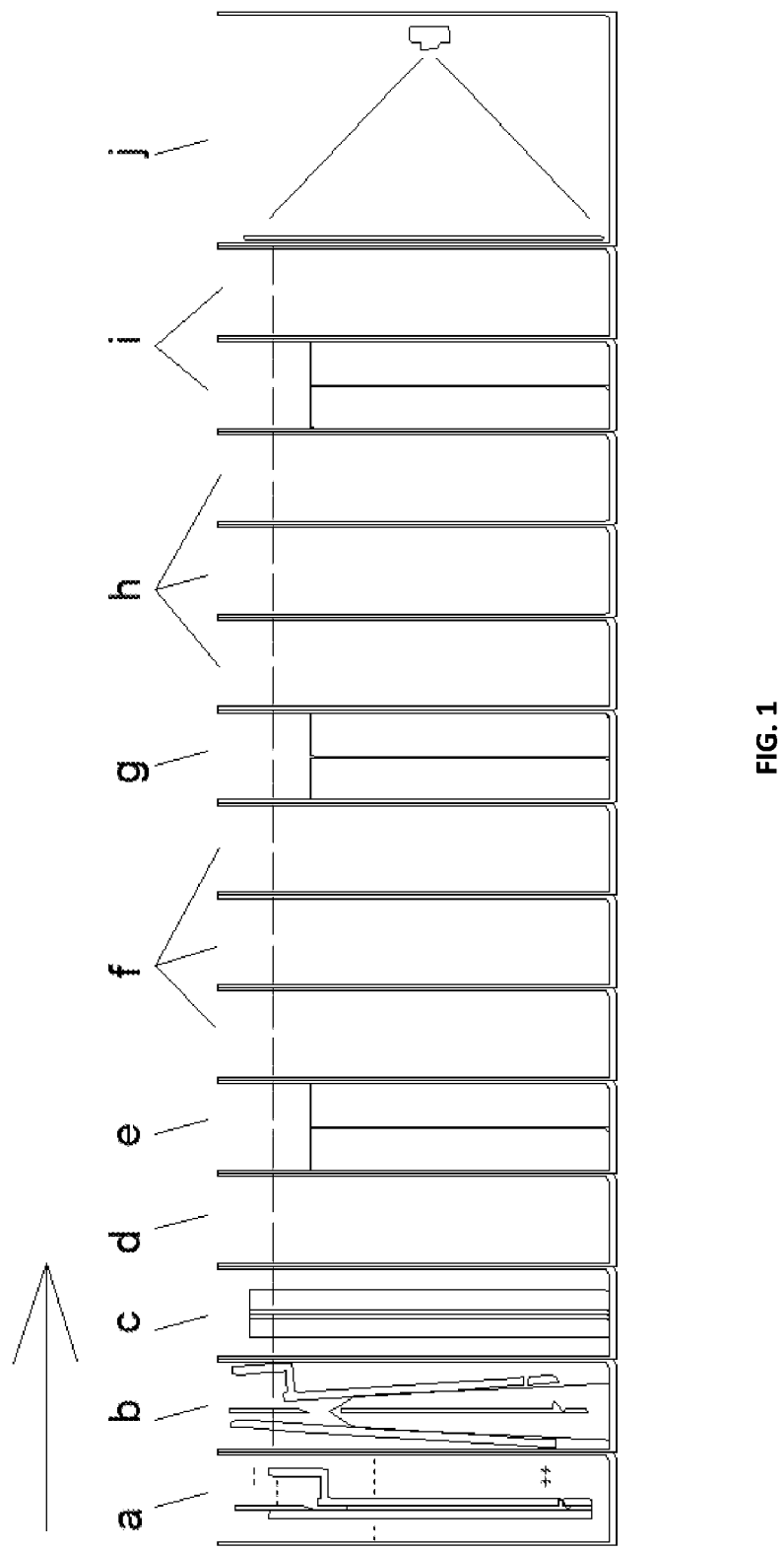
FIG. 1 shows an example work flow for an automated bioprocessing device.
Figure 2:
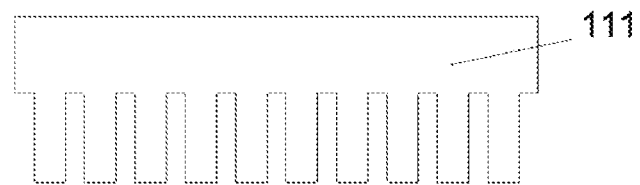
FIG. 2 is an illustration of an example front view of a gel comb 111.

The present disclosure relates to an improved apparatus and methods for processing biological samples using automation. Various modifications to the disclosed embodiment will be readily apparent to those skilled in the art and the principles herein may be applied to other embodiments and combination thereof. Although various components are discussed in the context of a particular initial design, it should be understood that the various elements can be altered and even replaced or omitted to permit other designs and functionality. Thus, the present disclosure is not intended to be limited to the embodiments shown but is to be accorded the widest scope consistent with the principles and features described herein. As used herein, the "present disclosure" or "present application" refers to any one of the embodiments of the disclosure described herein, and any equivalents thereof. Furthermore, reference to various feature(s) of the "present disclosure" or "present application" throughout this document does not mean that all claimed embodiments or methods must include the referenced feature(s).

The automated bioprocessing devices and automated bioprocessing methods disclosed herein include automated devices and methods for performing one or more protocols for processing biomolecules. In some embodiments, the bioprocessing device may include performing assays on biological samples mounted on microscope slides. In some embodiments, the bioprocessing device may include the use of labeled molecules, wherein the labels include, for example, immunofluorescence or fluorescent labels. In some embodiments, the protocols for processing biomolecules are dealing with biomolecules that are immobilized on a solid support, such as a blotting membrane with bound biomolecules. As such, the protocols can be protocols for processing Western blots (i.e., immunoblots), northern blots, or Southern blots. The automated bioprocessing devices and automated bioprocessing methods disclosed herein provide for automated bioprocessing that increase the efficiency and flexibility of persons operating such bioprocessing while providing performance that is at least as good as, if not better than similar manual processing.

NUMERALS

100 Gel-frame cassette
111 Gel comb

121 Gel-frame holding hole
122 Gel-frame
123 Protein loading well
124 Resolving gel
152 Electrophoresis cathode chamber
153 Back panel
154 Back panel bottom opening
155 Front panel
156 Gel
161 Wedge rod
162 Insert groove
163 T groove
164 T slide
165 Gel-frame holding column
211 Electrophoresis chamber
212 Cathode buffer
213 Electrophoretic anode-part solution
214 Cathode
215 Anode
311 Separation chamber
312 Wedge column
313 Hollow chamber
411 Membrane-frame side bar
412 Membrane-frame holding hole
413 nitrocellulose/polyvinylidene difluoride (PVDF) membrane
422 panel with openings
423 toothed opening
424 upper opening
425 lower opening
426 bump
511 Electroblotting chamber
512 Holding pad
513 Membrane-frame cassette
514 Gel-frame
611 Antibody incubation chamber
612 Pouch
613 Blocking chamber
614 Antibody solution
615 Membrane-frame
616 Membrane-frame in-between pouches
617 Washing chamber
618 Toothed protrusion
621 Washing solution
622 Rod-shaped protrusion
623 Pouch structure
625 Rope protrusion
631 Incubation-washing frame
632 Blotting membrane
633 Washing chamber
634 Protrusion
635 Washing membrane
a Gel electrophoresis
b Panel detachment
c Electroblotting
d First blocking
e Antibody incubation
f First washing
g Antibody incubation
h Second washing
i Fluorescence development
j Signal collection To appreciate the features and advantages of preferred apparatuses and methods in accordance with the present disclosure, the reader is referred to the appended FIGS. 1-22 in conjunction with the following discussion. It is to be understood that the drawings are diagrammatic and schematic representations only and are neither limiting of the scope of the present disclosure nor necessarily drawn to scale.

I. Bioprocessing Device

In a first aspect, a device is disclosed which provides for automated bioprocessing of biological samples. The bioprocessing device can take a variety of forms. The embodiments will be described below in conjunction with an automated device shown in FIG. 1. As shown in FIG. 1, the bioprocessing device may have a plurality of chambers a-j, each of which may perform different steps of a bioprocessing task, e.g., a Western blot procedure. The bioprocessing device, when running Western blot, may comprise a loading component for protein samples, an electrophoresis component for protein samples, an electroblotting component to transfer protein samples from a gel to a blotting membrane, an antibody-treatment component for the blotting membrane, a signal development component for the blotting membrane, and signal collection/output component. The principles of operation of the device are applicable to other types of automated bioprocessing devices according to the present disclosure.

Figure 3:
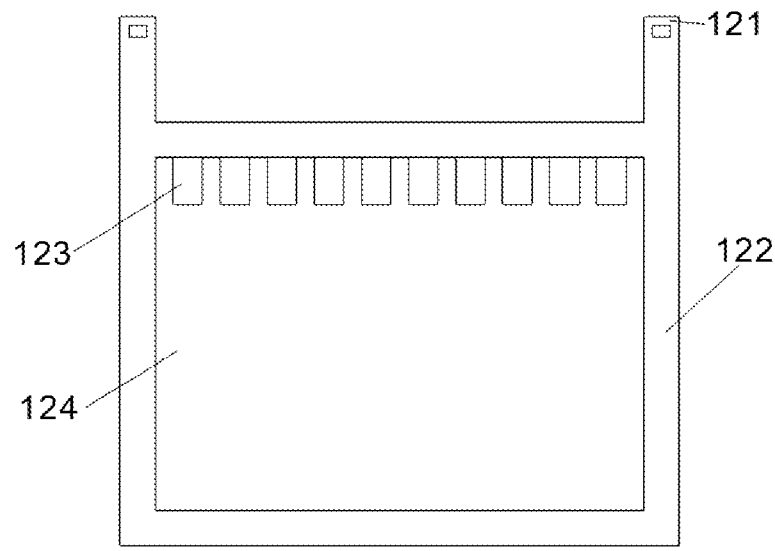
FIG. 3 shows an example front view of a gel-frame 122.

As shown in FIGS. 2-11, the bioprocessing device can automate processing steps in accordance with the present disclosure. The loading component for protein samples may be controlled by a processor, such as, for example, a computer processor. The loading component may handle multi-sample-loading. The electrophoresis component may comprise a power source, a gel-frame cassette 100, an electrophoresis chamber 211, and a separation chamber 311. The gel-frame cassette may comprise gel comb 111 having a comb structure with multiple teeth (FIG. 2), front panel 155, gel-frame 122, and back panel 153. In some cases, the gel comb may be made from plastics non-adhesive to the gel, i.e., plastics not forming covalent bond with the gel. The gel-frame 122 may be a frame with a hollow center (FIG. 3). Each of the two upper ends of gel-frame 122 may comprise a gel-frame holding hole 121 (FIG. 3), which may engage with and be controlled by a robotic arm. The gel-frame 122 of the gel-frame cassette 100 may form a composite with gel 156 through covalent bonds. The side of the gel-frame facing the gel 156 may comprise insert groove 162 which comprises a geometry shape that can facilitate the formation of the composite with gel 156. The front panel 155 and back panel 153 of the gel-frame cassette may be removed from the rest of the gel-frame by a robotic arm. The material of the gel-frame 122 may comprise different surface functional groups that improve or facilitate the formation of the composite between the gel-frame and the gel. The gel 156 may be sodium dodecyl sulfate-polyacrylamide gel electrophoresis (SDS-PAGE) gel, or other gel for electrophoresis.

Figure 4:
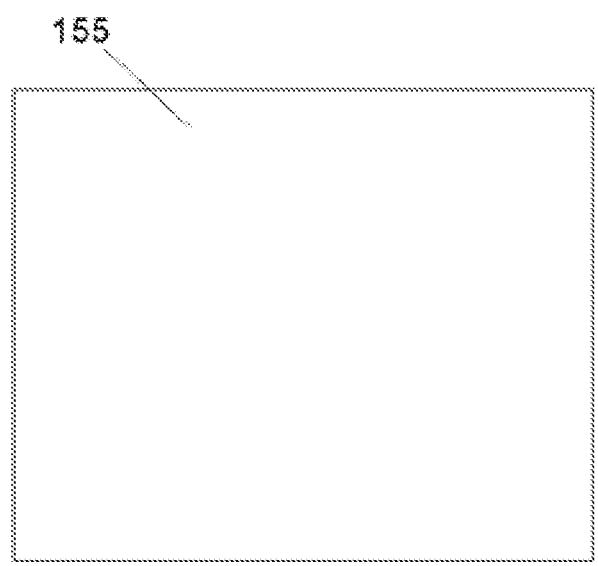
FIG. 4 shows an example front view of a front panel 155.
Figure 5:
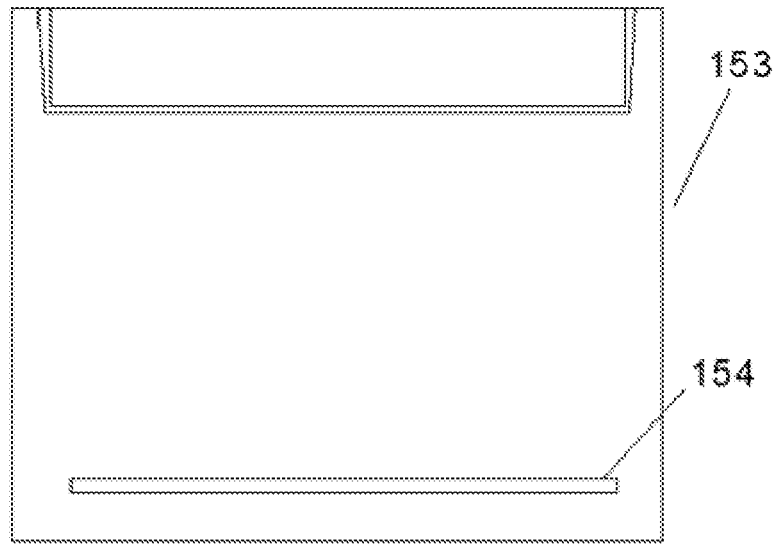
FIG. 5 shows an example front view of a back panel 153.
Figure 6:
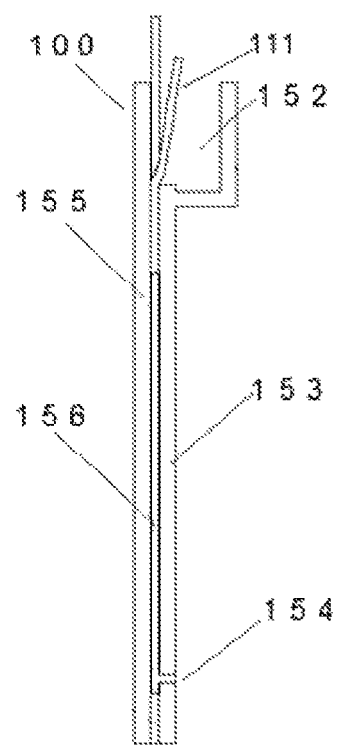
FIG. 6 shows an example section view of a gel-frame cassette 100.

The front panel 155 and the back panel 153 may be glass or plastics coated with a hydrophilic layer. The front panel 155 and the back panel 153 may be thin and pliable glass or thin plastics coated with a hydrophilic layer. The front panel 155 may be a rectangular shape (FIG. 4). The back panel 153 may comprise an expanded upper portion (FIGS. 5 and 6), which, when combined together with the gel-frame 122 and the front panel 155, form an electrophoresis cathode chamber 152 to hold electrophoretic solutions. The back panel 153 may comprise a back panel bottom opening 154 at the lower part of the back panel 153 (FIGS. 5 and 6). The back panel bottom opening 154 may be a rectangular shape that can be sealed by an adhesive tape (FIG. 5).

The method to form a composite of the gel-frame 122 with the gel 156 may be a mechanical method strengthened by a chemical method. When the gel 156 is formed by polymerization, it may form covalent chemical bonds with the gel-frame 122 to afford the composite with the gel-frame 122.

Figure 7:
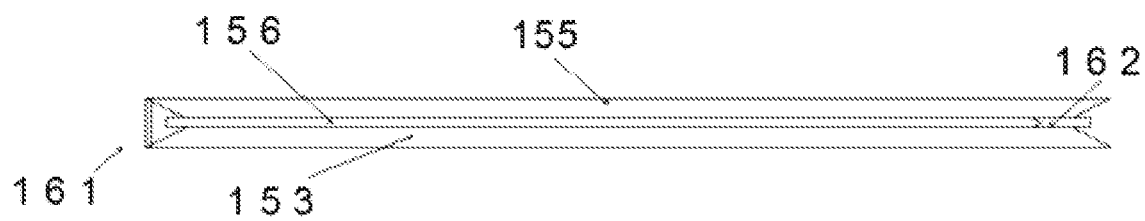
FIG. 7 shows an example bottom view of the gel-frame cassette 100 shown in FIG. 6.

The left and right sides of the gel-frame cassette, enclosed by the front panel 155, back panel 153 and the sides of the gel-frame 122, may form a W-shaped gap structure, into which a wedge rod 161 with a matching shape can insert (FIG. 7). When the wedge rod 161 with a matching shape is inserted into the W-shaped gap structure, it can remove the front panel 155 and the back panel 153 from the gel-frame cassette 100, leaving behind the gel-frame 514.

Figure 11:
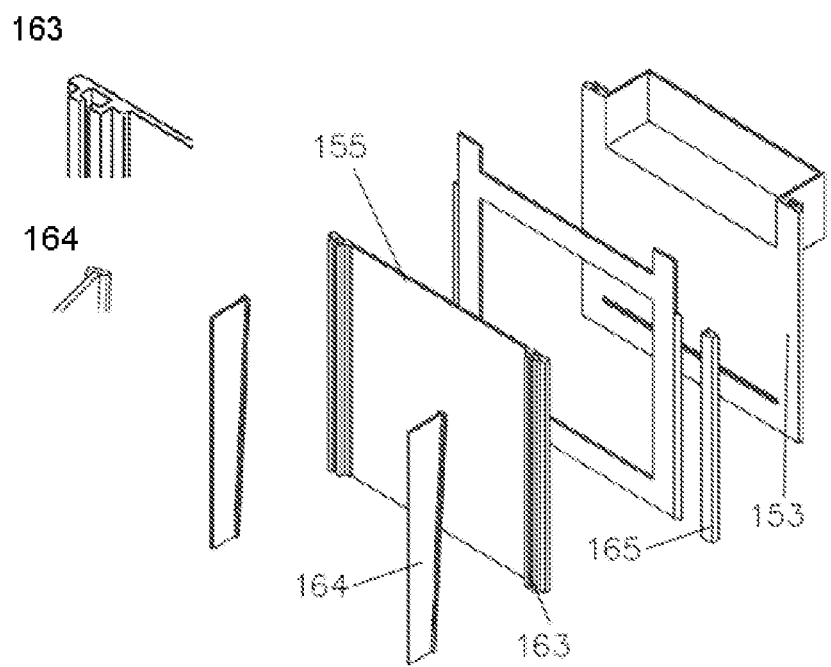
FIG. 11 provides an exploded view of another separation process for a gel-frame with enlarged view of T groove 163 and T slide 164.

In some cases, the separation of the panels from the gels can be accomplished by a method using a pre-installed T grove. In some cases, the left and right sides of the front panel 155 and back panel 153 may comprise pre-installed T groove 163 (FIG. 11). When a robotic arm which carries the gel-frame 100 and presses it down, pre-installed T slide 164 in a separation chamber 311 may slide into the T groove 163 on the front panel 155 (FIG. 11), thereby removing or separating the front panel 155 and the back panel 153 from the gel-frame 514, while the gel-frame 155 may remain in the middle position held by the gel-frame holding column 165 (FIG. 11). Subsequently, the robotic arm moves upward together with the gel-frame 514; and the front panel 155 and the back panel 153 may be left in the separation chamber.

Figure 9:
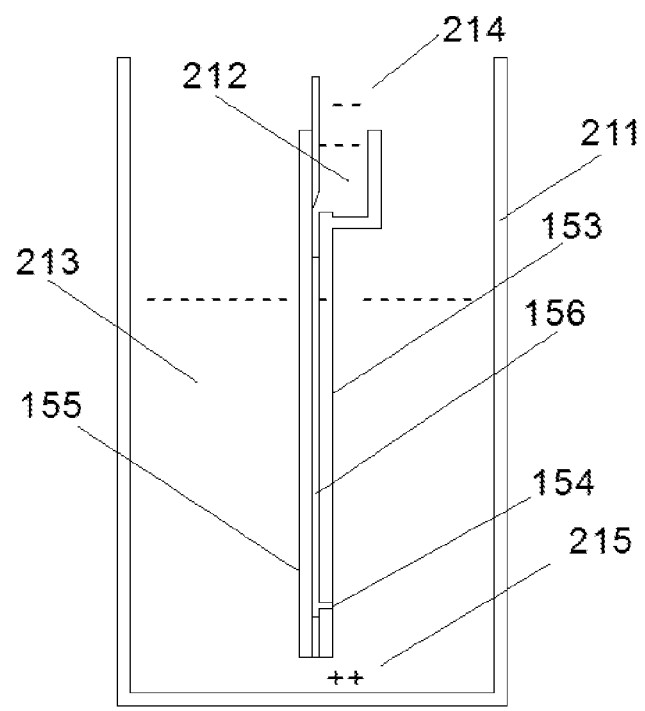
FIG. 9 is an example of electrophoresis process according to the present disclosure.

In some cases, the electrophoresis chamber 211 may be a container containing an electrophoretic anode-part solution 213 and an anode 215 at the bottom of the chamber (FIG. 9). The cathode 214 may be at the upper end of the chamber 211 (FIG. 9). The cathode 214 may be placed inside the electrophoresis cathode chamber 152. After plugged in, the electrophoresis may be performed on the gel.

Figure 10:
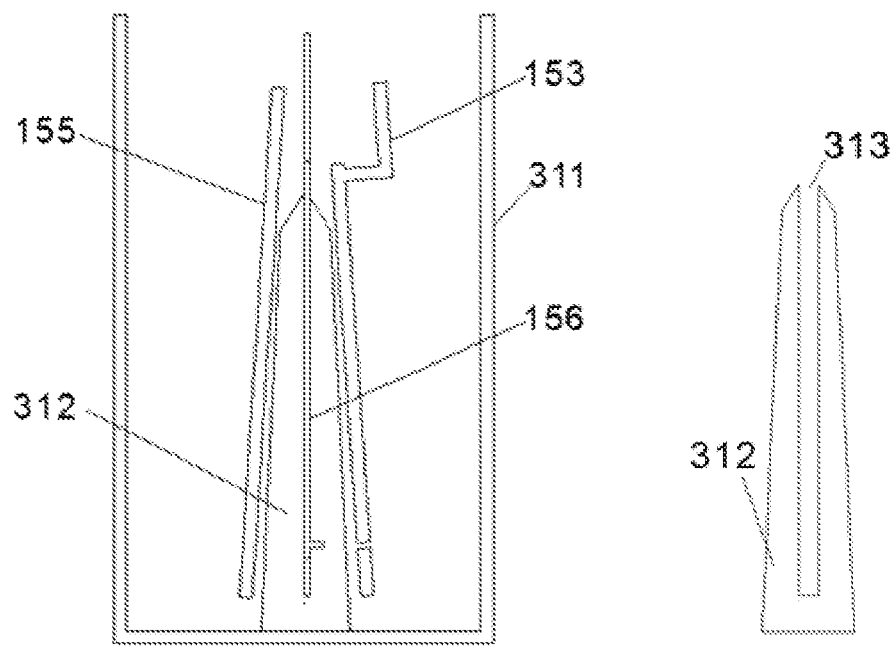
FIG. 10 shows an example of a separation chamber and the structure of an example wedge column 312.

In some cases, the separation chamber 311 may have wedge column 312 at the bottom of the separation chamber 311 (FIG. 10). The wedge column 312 may remove the front panel 155 and the back panel 153 from the gel-frame cassette 100. The wedge column 312 may comprise hollow chamber 313 for the separation of the gel-frame 156 from the front panel 155 and the back panel 153 (FIG. 10).

Figure 12:
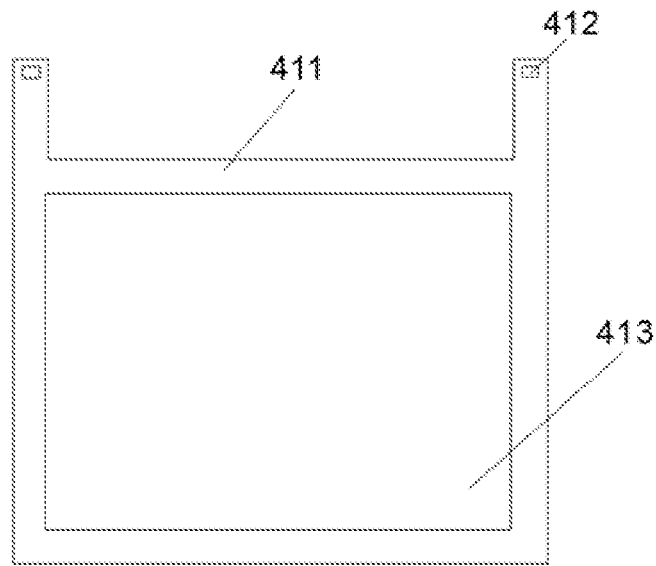
FIG. 12 shows an example of a membrane-frame according to the present disclosure.

In some cases, the electroblotting component to transfer protein samples from the gel to a blotting membrane may comprise membrane-frame cassette 513 and electroblotting chamber 511. The membrane-frame cassette 513 may comprise a membrane-frame composite with a blotting membrane fixed inside the side bars. The fixing method can be mechanical, heating, polymerization or chemical methods. The blotting membrane may be the nitrocellulose/polyvinylidene difluoride (PVDF) membrane, which can bind proteins. The membrane-frame cassette 513 may be a rectangular shape and its side bars on the left and right sides may protrude above the membrane-frame top bar, with the membrane-frame holding holes 412 on the top part of the protruding side bars (FIG. 12). The membrane-frame holding hole 412 can interact with a robotic arm. The membrane-frame cassette 513 may be a cassette that enables a blotting membrane to be transported and/or controlled by a robotic arm. Using the robotic arm to control the transport of the blotting membrane may facilitate electroblotting, incubation of the blotting membrane with antibodies, washing and collecting signals.

The electroblotting chamber 511 may contain an electroblotting solution and may allow the insertion of gel-frame 514 (FIG. 13) in the electroblotting chamber 511. The membrane-frame cassette 513 may be pre-installed into the electroblotting chamber 511. The membrane-frame cassette 513 may be confined at one side of the electroblotting chamber 511, may move vertically, but may not move horizontally. In addition, there are holding pads 512 inside the electroblotting chamber 511. These holding pads 512 may be controlled by a computer. The holding pad may use electromagnetic or mechanical force to hold subjects.

The antibody-treatment component (FIG. 14) may comprise: an antibody incubation chamber 611 comprising pouches 612, a blocking chamber 613 which may be pre-loaded with antibody solution 614 and may hold the membrane-frame 615, and a washing chamber 617. The antibody incubation chamber 611 comprises two pouches 612, each of which is attached to the bottom of the antibody incubation chamber 611. There may be a gap between the two pouches 612 such that the membrane-frame cassette 513 may insert into the gap. Further, the pouch 612 is inflatable in that when the pouch 612 is inflated, solution or solvent may be forced to move to the upper portion of the antibody incubation chamber 611.

Figure 15:
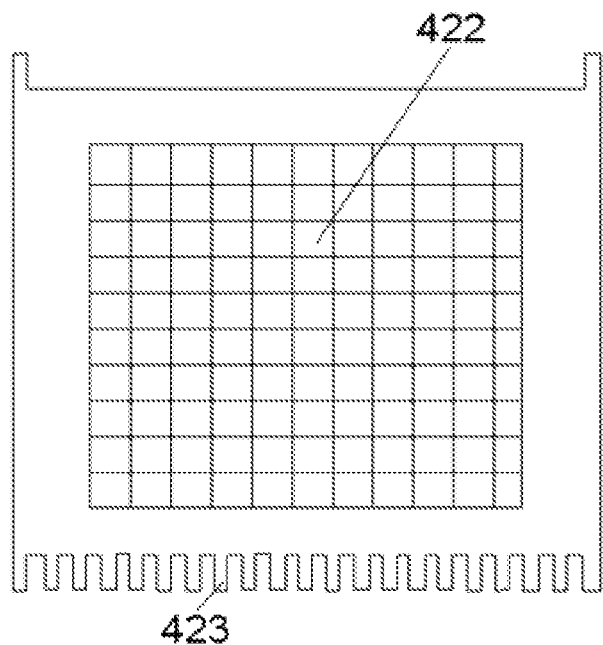
FIG. 15 shows an example of the front/back panel of another membrane-frame cassette with hollow chamber in the middle according to the present disclosure.
Figure 16:
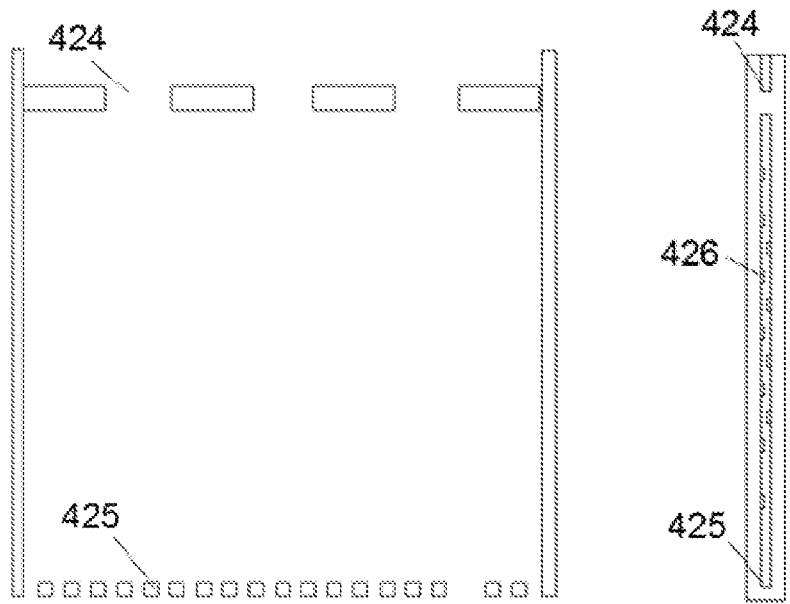
FIG. 16 depicts two example section views of the membrane-frame cassette shown in FIG. 15.

As an alternative, the membrane-frame cassette 513 may be in other forms or combinations, including, for example, center-hollow membrane-frame cassette (FIGS. 15 and 16). The center-hollow membrane-frame cassette may be a center-hollow structure, i.e., a container with openings, which may hold the blotting membrane inside the structure/case. Since there are multiple openings on the front and back panels of the case and openings on the top and bottom panels of the case, solvent/solution may enter into and exit out of the container through the front panel, the back panel, the top opening, and the bottom opening. Further, the blotting membrane may flow or move within the case. There may be bumps 426 on the inner face of the back panel and the inner face of the front panel. The front/pack panel 422 of the enter-hollow membrane-frame cassette may have a plurality of openings to allow solution/solvent to pass through. There may be toothed openings 423 on the bottom of the membrane-frame cassette. When the blotting membrane is at the lowest position inside the membrane-frame cassette, an external object may enter into the membrane-frame cassette through the toothed opening 423 and agitate the blotting membrane.

Figure 17:
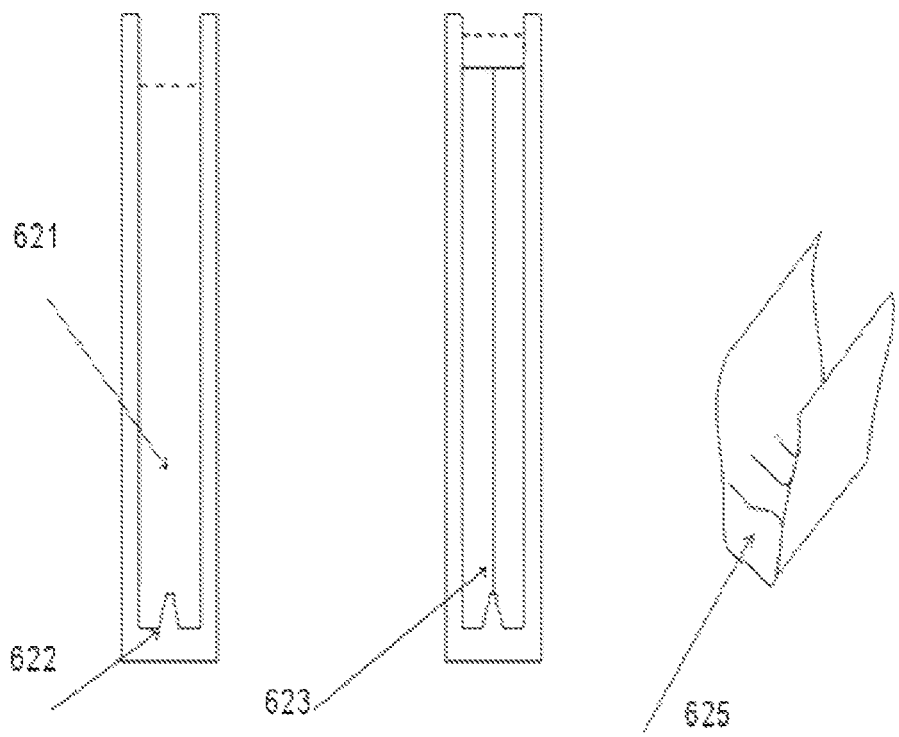
FIG. 17 shows example section views of two washing chambers for the membrane-frame cassette.

In some cases, each of the blocking chamber 613, the antibody incubation chamber 611, and the washing chamber 617 of the membrane-frame cassette 513 may comprise a flat bottom. In other cases, each of the blocking chamber 613, the antibody incubation chamber 611, and the washing chamber 617 of the center-hollow membrane-frame cassette may comprise toothed protrusions 618, which agitates the blotting membrane inside the center-hollow membrane-frame cassette. If the chamber comprises a pouch 623, rope protrusions 625 may be used to agitate the blotting membrane (FIG. 17).

The signal development component for the blotting membrane, and the signal collection/output component may comprise multiple working chambers (FIG. 1).

In some cases, there may be multiple chambers doing the same or similar processing step. For example, there may be multiple washing chambers in a device of the present disclosure. In some cases, certain part of an individual chamber or component may be removed or be duplicated in a device of the present disclosure. In some cases, certain component(s) may be removed or switched positions with another component. In some cases, each chamber is modular and can be rearranged according to the needs of the technician.

II. Methods of Bioprocessing

In one aspect, the present disclosure also disclose methods of bioprocessing for automation of Western blot, comprising the steps of electrophoresis, electroblotting, antibody incubation, blocking, washing, signal development, and signal collection. In some embodiments, the present disclosure discloses methods of producing certain part of the device or certain part of a component, such as, for example, gel-frame cassette, and membrane-frame cassette.

Step 1. An assembly of the gel-frame 122, front panel 155, and back panel 153 may be provided according to FIGS. 3-6. The assembly may be taped at the left and right sides and at the bottom while leaving a space in-between the front and back panels for gel formation. Then starting materials for gel may be added to the space in-between the front and back panels. A gel comb 111 may be slid in at an angle (FIG. 6) at the top of the assembly to produce loading wells for protein samples. The gel may be polymerized, thereby producing the gel-frame cassette 100.

Step 2. The gel-frame cassette 100 may be placed into the electrophoresis chamber 211 (FIGS. 6 and 9). An electrophoretic anode-part solution 213 may be added to the electrophoresis chamber 211. An anode may be installed at the bottom of the electrophoresis chamber 211. A cathode buffer 212 may be added to the electrophoresis cathode chamber 152 which is formed in-between the front panel 155 and the back panel 153. A cathode may be installed at the electrophoresis cathode chamber. Then the gel comb 111 may be removed from the gel-frame cassette 100. Protein samples may be added to the sample wells either manually or mechanically. Electrophoresis may be performed under the control of a processor, such as, for example, a computer processor.

Step 3. As shown in FIGS. 9 and 10, after the electrophoresis is completed, a processor may send commands to a robotic arm which may be placed above the electrophoresis chamber 211 and the gel-frame cassette 100. The robotic arm may move down and engage with the gel-frame holding holes 121 (FIG. 3) to control the movement of the gel-frame cassette 100. The robotic arm may lift the gel-frame cassette 100 upwards and out of the electrophoresis chamber 211, transfer the gel-frame cassette 100 above the separation chamber 311 (FIG. 10). At the bottom of the separation chamber 311 here may be a wedge column 312 at the left side and right side, respectively, of the separation chamber 311 (FIG. 10). The wedge column 312 may be narrower at the top than at the bottom. The wedge column 312 may comprise a hollow chamber 313 in the middle (FIG. 10) to receive and restrict the movement of the gel-frame 122 and the gel 156 inside the hollow chamber 313 when the gel-frame cassette 100 is moving vertically inside the separation chamber 311. When the robotic arm holding the gel-frame cassette 100 is moving downward, the wedge column 312 may engage with the gel-frame holding column 165 (FIG. 11) from the bottom side of the gel-frame cassette 100, and may push the front panel 155 and the back panel 153 to disengage from the centered gel-frame 122 of the gel-frame cassette 100. The robotic arm may move up and down multiple times such that both the front panel 155 and the back panel 153 are no longer attached to the gel-frame 122. The remaining gel-frame 122 and gel 156 may produce gel-frame 514 to be processed later. In some cases, the front panel 155 and the back panel 153 may be left in the separation chamber 311. In some cases, the preformed T groove 163 and T slide 164 (FIG. 11) may be used to remove the front panel 155 and the back panel 153 from the gel-frame 514. For example, the T slide 164 may slide in and engage with the T groove 163 (which is formed on the sides of the front panel 155 and the back panel 153). As shown in FIG. 10, the T slide 164 is wider at the top than at the bottom. Therefore, after the T slide in from the bottom of the gel-frame cassette 100 and move upwards, the back panel 153 and the front panel 155 may be pulled apart and leave the gel-frame 514 free from both panels. Again the robotic arm may move the gel-frame cassette 100 when the T slide 164 is engaging with the T groove 163.

Figure 13:
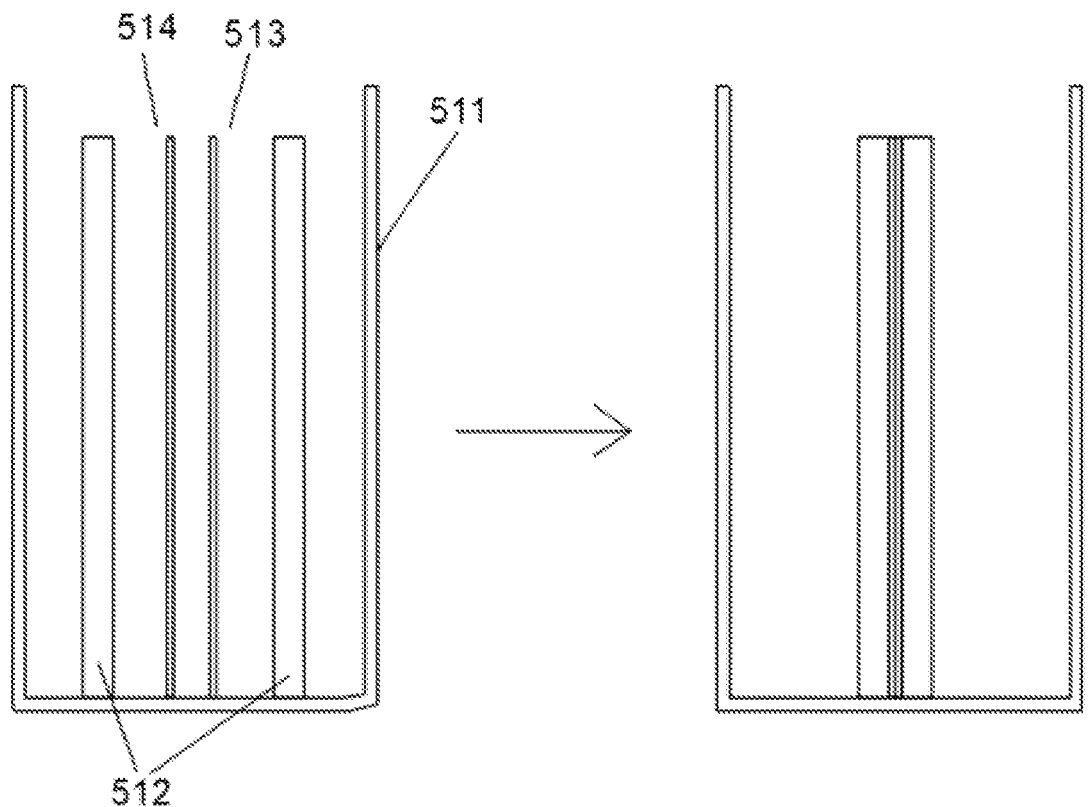
FIG. 13 provides an example electroblotting process according to the present disclosure.

Step 4. The robotic arm may lift the gel-frame 514 out of the separation chamber 311 and move it above the electroblotting chamber 511 (FIG. 13). The robotic arm may lower the gel-frame 514 into the electroblotting chamber 511 and place it in-between a holding pad 512 and a membrane-frame cassette 513. The robotic arm may move horizontally to push the gel-frame 514 close to the membrane-frame cassette 513. Holding pads 512 may be controlled by a processor, such as, for example, a computer processer, to move toward each other and toward the center of the electroblotting chamber 511 under electromagnetic or mechanical forces such that the gel-frame 514 and the membrane-frame cassette may be pressed together due to the pressing force from the holding pads 512. Then electroblotting process may transfer protein samples from the gel to the blotting membrane inside the electroblotting chamber. After the completion of the electroblotting process, the holding pads 512 may move away from each other and back to their original positions. The robotic arm which holds the gel-frame 514 may move horizontally such that the gel-frame 514 may separate from the membrane-frame cassette 513. Subsequently, the robotic arm may disengage from the gel-frame 514, move up, move above the membrane-frame cassette, move down, and engage with the membrane-frame holding holes 412. Then the robotic arm may move the membrane-frame cassette 513 out of the electroblotting chamber 511 to other component of the devices of the present disclosure, including, for example, the blocking chamber 613, the antibody incubation chamber 611, the washing chamber 617, and other chambers for signal development or signal collection. In some cases, when a blotting membrane without side arms attached (for the robotic arm to hold) is used, a center-hollow membrane-frame cassette (FIGS. 15 and 16) may be used to hold the blotting membrane. In some cases, the blotting membrane or the center-hollow membrane-frame cassette may be processed in a washing chamber with toothed protrusions 618, rod-shaped protrusion 622 (FIG. 17), or other elements that may agitate the membrane during the washing/incubation processes. In some cases, the blotting membrane or the center-hollow membrane-frame cassette may be processed in a chamber with pouches 612 (FIGS. 14 and 16) and rope protrusions 625 (FIG. 17). In some cases, the antibody incubation and membrane washing processes may use a combination of the chambers in the present disclosure.

Step 5. After the signals are developed in the signal development chamber, the signals from the blotting membrane may be collected or recorded in a signal collection chamber by a recording device, such as, for example, an electronic device, for signal collection and analysis to complete the Western blot.

In some embodiments, the gel-frame cassette may provide controlled movement of the gel which is soft and pliable by a robotic arm. In some cases, the separation of the gel from the gel-frame cassette may be performed by mechanical force within the separation chamber rather than by the hands of a technician. The robotic arm or other electronically controlled parts of the present disclosure may move the gel-frame from one chamber to another and conduct various operations, including, for example, placing the gel-frame close to the blotting membrane for electroblotting. In some cases, production of the gel-frame may be conducted to form covalent chemical bonds between the gel and the holding frame. For example, the surface of the frame may be chemically treated to enhance covalent bond formation with the polymerizing gel. Covalent bonding between the gel and the frame may enhance the stability of the formed gel-frame during bioprocessing.

Figure 8:
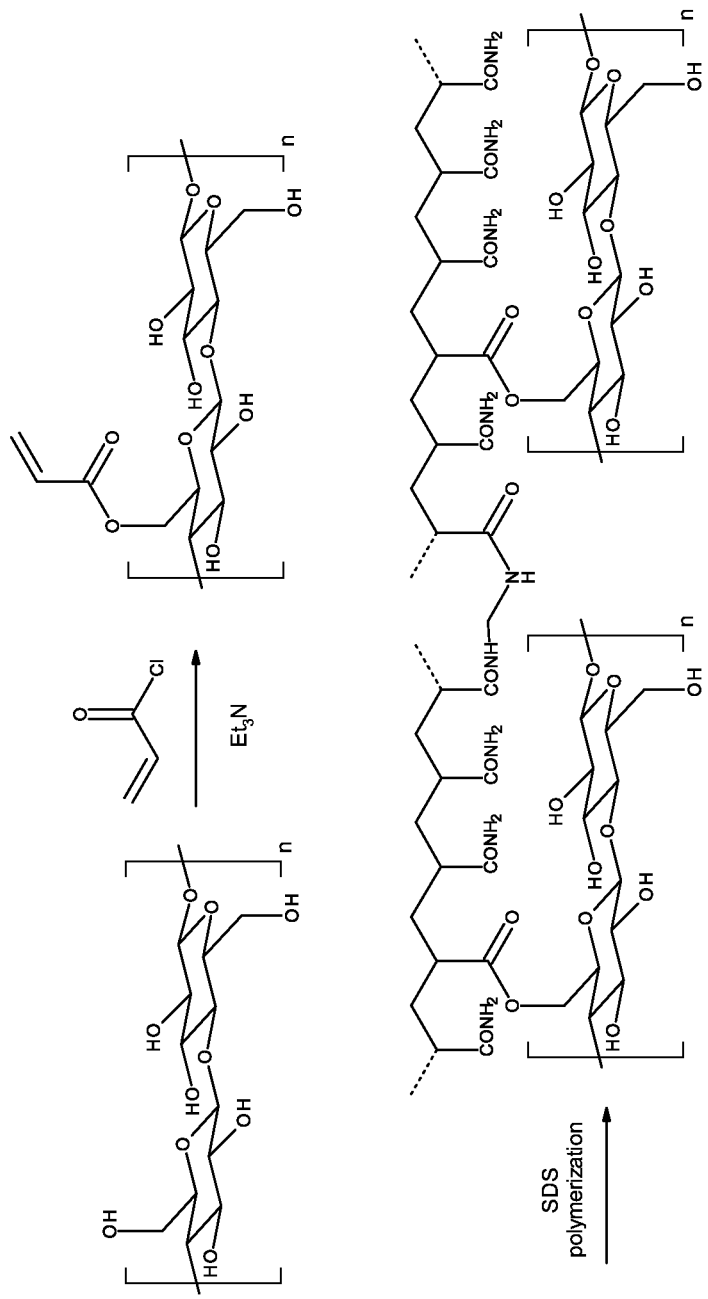
FIG. 8 shows an example chemical process of to assemble a gel-frame according to the present disclosure.

FIG. 8 shows one of the chemical treatments for the formation of the gel-frame according to the present disclosure. In some cases, the frames of the gel-frame, such as, for example, the side bar of the gel-frame, may comprises a plurality of chemical functional groups for bond formation. For example, the materials for the frame may comprise fibers comprising a plurality of hydroxyl groups, such as, for example, hydroxyl groups on a carbohydrate molecule. The carbohydrate molecule may be a polymer, such as, for example, a polysaccharide. In some cases, the polysaccharide may be cellulose. In some cases, the cellulose may react with acryloyl chloride under basic conditions to produce cellulose bonded with acryloyl groups through hydroxyl groups on the cellulose, such as, for example, primary hydroxyl groups. After such treatment, the surface of the frame may comprise a plurality of acryloyl groups, whose unsaturated double bonds may undergo polymerization reactions via a radical reaction mechanism. During the SDS-PAGE gel polymerization, at least a portion of the surface acryloyl groups on the frame may form covalent bonds with the gel. These covalent bonds between the frame and the gel, together with the intertwining polymer chains associated with such covalent bonds, may improve the mechanical stability of the gel-frame, thereby allowing the robotic arm to control and move the gel according to the present disclosure.

In some embodiments, membrane-frame cassette may be controlled by a robotic arm during various bioprocessing steps for the blotting membrane in the membrane-frame cassette, including, for example, blocking step, incubation step, washing step, in different chambers. The membrane-cassette, when controlled by the robotic arm, may move vertically within a chamber to facilitate relative movement between the membrane and the solution/solvent. In some cases, such vertical movement of the membrane may be similar to shaking the membrane. In some cases, the membrane-frame cassette may be moved horizontally to place the membrane-frame cassette at different positions within a chamber. The time for the membrane-frame cassette to stay in each chamber and interact with different solutions/solvents for each processing step may be determined according to standard Western blot protocols. In some cases, the antibody solution may be placed in individual chambers. In some cases, if needed, the antibody solution may be reused. According to FIGS. 16-19, methods of the present disclosure may reduce the amount of the antibodies used in the incubation step.

Figure 14:
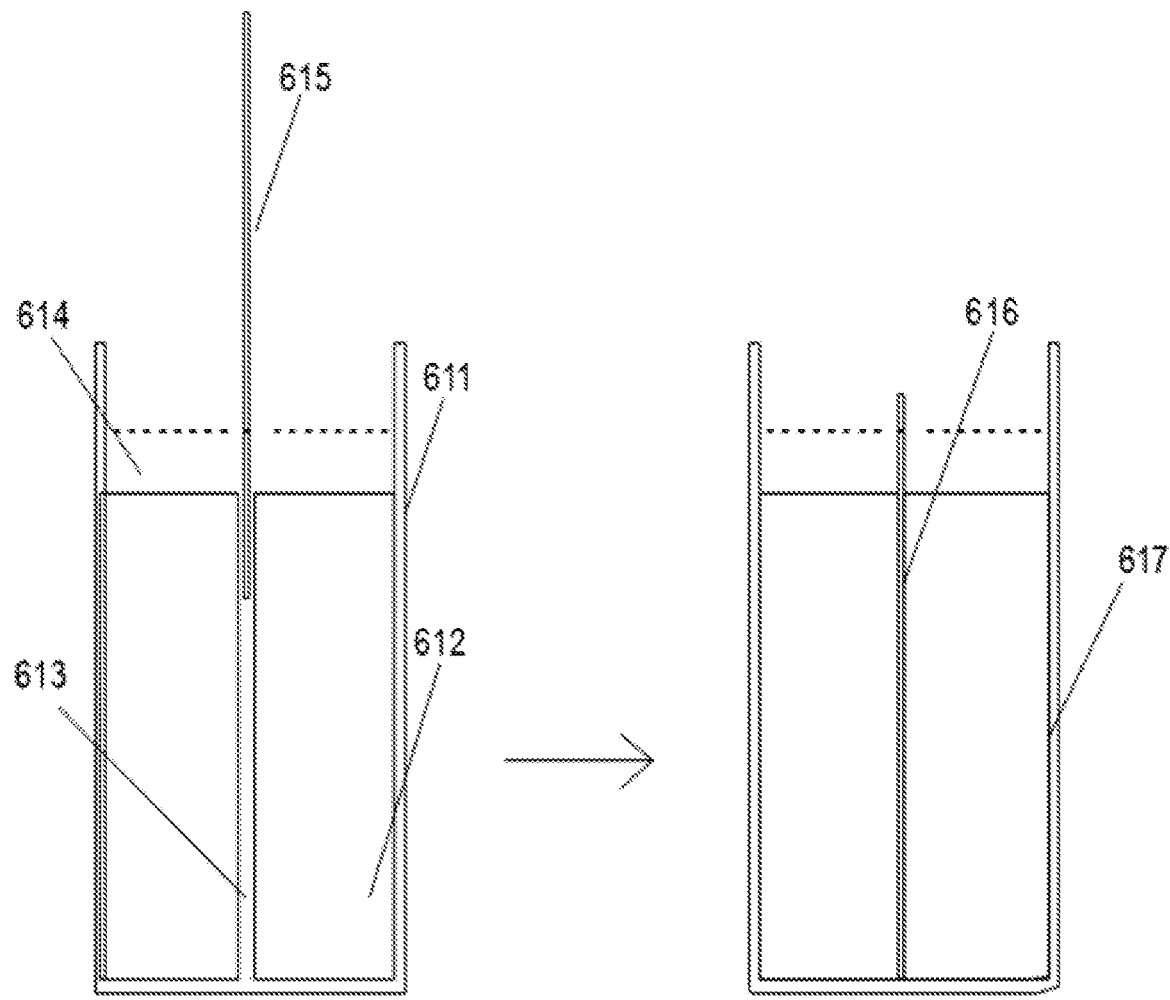
FIG. 14 depicts an example antibody incubation process of the membrane-frame according to the present disclosure.

As shown in FIG. 14, an antibody incubation chamber 611 may comprise pouches 612 attached to the bottom of the antibody incubation chamber 611. In some cases, the pouch may be inflatable. In some cases, there may be a blocking chamber 613 in-between the pouches 612. In some cases, the blocking chamber 613 may accommodate and receive membrane-frame 513. In some cases, the pouches 612 may be filled with fluid, such as gas or liquid. In some cases, an antibody solution 614 may be added to the antibody incubation chamber 611. When adding the antibody solution 614, the pouches 612 may be inflated, reduce the volume of the blocking chamber 613 such that most of the antibody solution 614 stays on the upper portion of the antibody incubation chamber 611 and above the pouches 612. Subsequently, the robotic arm may move the membrane-frame 615 above the antibody incubation chamber 611, move the membrane-frame 615 into the antibody incubation chamber 611, through the antibody solution 614 on the upper portion of the antibody incubation chamber 611, and into the blocking chamber 613. When the membrane-frame 615 is passing through the antibody solution 614, both sides of the blotting membrane may interact with the antibody solution, thereby being incubated with the antibody solution thoroughly.

Figure 18:
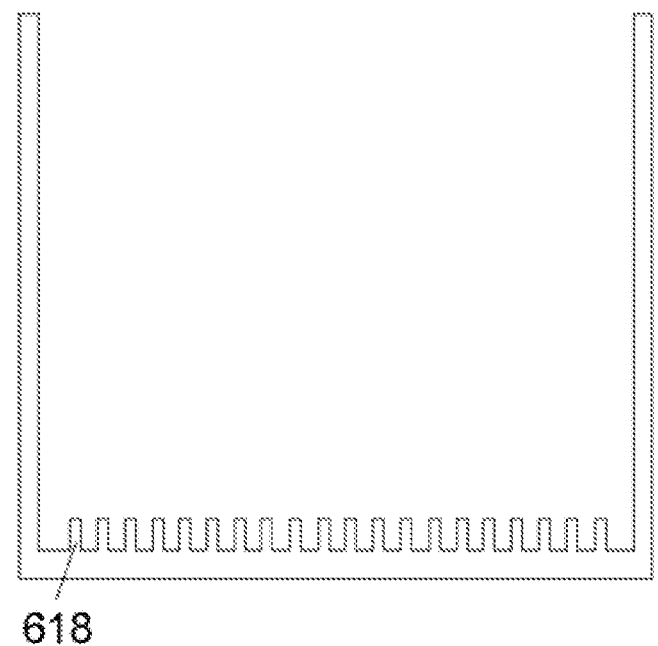
FIG. 18 provides an example section view of the washing chambers shown in FIG. 17.
Figure 19:
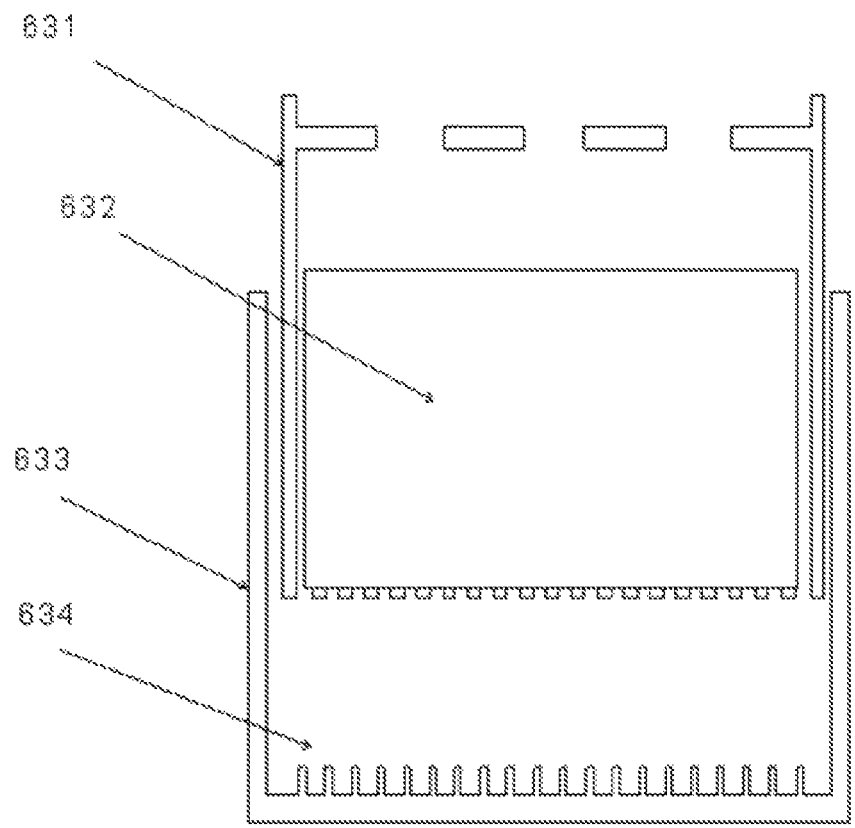
FIG. 19 depicts an example process of antibody incubation using the membrane-frame of the present disclosure.
Figure 20:
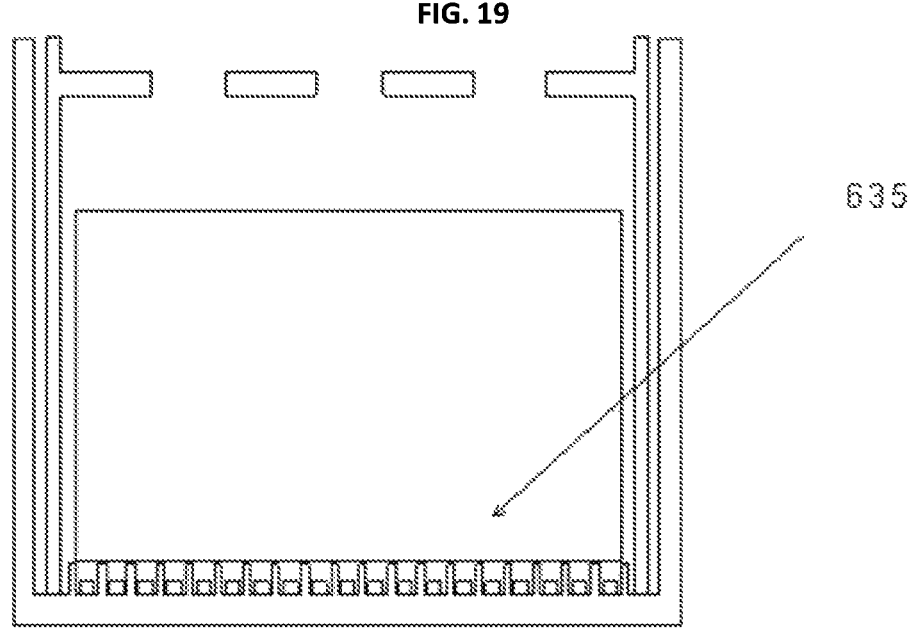
FIG. 20 shows an example process of shaking blotting membrane during antibody incubation using the membrane-frame of the present disclosure.

In some cases, blotting membrane may not have a frame attached. In some cases, blotting membrane without a frame may be placed into a center-hollow membrane-frame cassette (FIGS. 15 and 16). In some cases, the center-hollow membrane-frame cassette with blotting membrane inside may undergo processing steps, including, for example, blocking, antibody incubation, and washing. When the center-hollow membrane-frame cassette is used, the corresponding blocking chamber, antibody incubation chamber, and washing chamber may install rod-shaped protrusions 622 (FIG. 17) or toothed protrusion 618 (FIG. 18). After the chamber is filled with solution/solvent, when the center-hollow membrane-frame cassette is at higher position (FIG. 19) above and not contacting the rod-shaped protrusions 622 or toothed protrusion 618, the blotting membrane may locate at the lower portion of the center-hollow membrane-frame cassette (FIG. 19). When the center-hollow membrane-frame cassette is lowered to the bottom portion of the chamber, the rod-shaped protrusions 622 or toothed protrusion 618 (FIG. 20) may protrude into the center-hollow membrane-frame cassette from openings on the bottom side of the center-hollow membrane-frame cassette, push the blotting membrane upward (FIG. 20), thereby agitating the blotting membrane.

As shown in FIG. 17, a pouch structure 623 may be used to save the amount of antibody used. In some cases, at the bottom of the pouch structures 623 and in the space in-between the pouches 623, there may be rope protrusions 625. The rope protrusion 625 may perform similarly to a toothed protrusion, such as the rod-shaped protrusion 622, to move the membrane upward within the center-hollow membrane-frame cassette.

Figure 21:
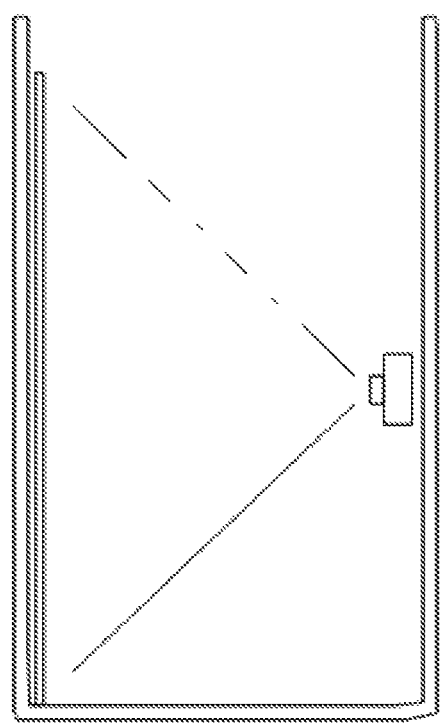
FIG. 21 provides an example of signal collection according to the present disclosure.
Figure 22:
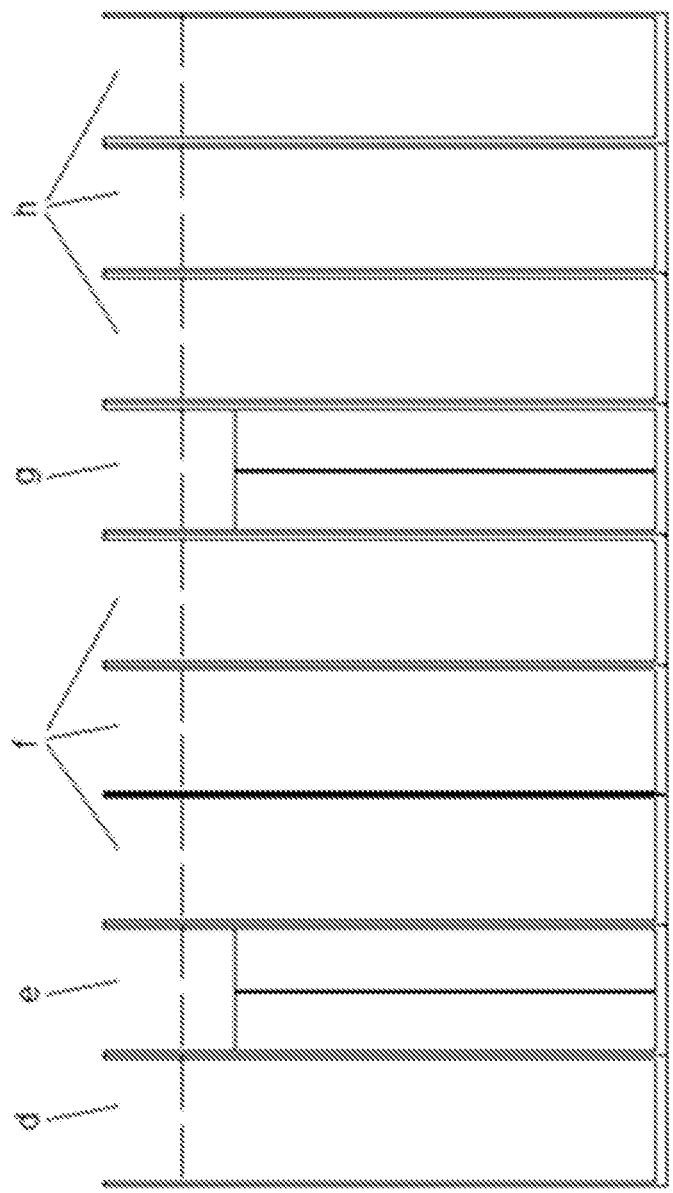
FIG. 22 depicts an example process for a membrane-frame cassette with hollow chamber in the middle according to the present disclosure.
Figure 22:
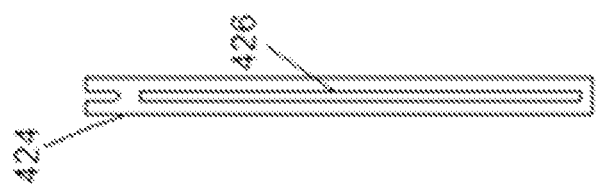

As shown in FIGS. 21-22, the secondary antibody for the incubation of membrane-frame cassette may be an antibody tagged by an enzyme, or an antibody labeled with fluorescence. When the antibody incubation and washing steps are completed, the robotic arm may move the membrane-frame cassette into the signal development chamber and collection chamber. If an antibody labeled with fluorescence is used, the membrane-frame cassette may be transferred to signal collection chamber, exposed to light, be scanned for signals.

When the secondary antibody is tagged with an enzyme, the Enhanced chemiluminescence (ECL) method may be used for signal development and collection. In some cases, an ECL chamber with pouches may be used and ECL reagent may be added to the solution/solvent of the chamber. Subsequently the membrane-gel cassette may be incubated and agitated inside the ECL chamber, then moved into the signal collection chamber for the electronic device to collect signals.

As shown in FIG. 1, the bioprocessing method of the present disclosure may comprise: A gel frame cassette may be produced using the methods in the present disclosure; a robotic arm may engage with and move the gel-frame cassette; protein samples may be added manually or automatically; and electrophoresis may be performed on the protein samples loaded onto the gel in (a). The robotic arm may separate the front panel and back panel of the gel-frame cassette in the separation chamber, thereby producing a gel-frame in (b). The protein samples from the gel may be electrotransferred to the membrane in the electroblotting chamber in (c). The gel and the blotting membrane may be separated. The robotic arm may transfer the blotting membrane among multiple chambers, thereby completing blocking of the blotting membrane in (d). The blotting membrane may incubate with antibodies in e and g, be washed in f and h, and have the signals developed in (i). The signals may collected by electronic device in (j), thereby completing the Western blotting.

In some embodiments, the device of the present disclosure may include different combinations of each disclosed component. In some cases, a device of the present disclosure may perform antibody incubation and washing only, or any combinations or selections of the Western blot steps. As shown in FIG. 22, a device of the present disclosure may comprise a center-hollow membrane-frame cassette (FIGS. 15 and 16) 424. The corresponding bioprocessing steps for the center-hollow membrane-frame cassette 424 may comprise: blocking (d), antibody incubation (e, g), and washing (f, h). The corresponding chambers for processing the center-hollow membrane-frame cassette 424 are shown in FIG. 22.

In some cases, the advantages of the devices, systems and methods of the present disclosure may include:

(1) Use a robotic arm to manipulate and control the movement of the gel-frame cassette, the gel-frame, and/or the membrane-frame cassette. Automate the movement of the gel and/or the blotting membrane from one chamber to another, and agitate the gel and/or the blotting membrane within each chamber.

(2) Employ the robotic arm, the gel-frame cassette, the membrane-frame cassette, and a plurality of processing chambers for the corresponding steps for the automation, including, for example, automated electrophoresis, automated removal of panels from the gel, automated electroblotting from the gel to the blotting membrane, automated antibody incubation of the blotting membrane, automated signal development and signal collection.

(3) Use center-hollow membrane-frame cassette for a standalone blotting membrane in the antibody incubation, washing, and blocking steps of Western blot.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

We claim:

1. A gel-frame cassette for an automated bioprocessing device, comprising:
    a gel-frame comprising:
        a front face,
        a back face,
        a frame comprising:
            two vertical side bars, each comprising a gel-frame holding hole,
            a top bar connecting the two vertical side bars,
            a bottom bar connecting the two vertical side bars and
            a hollow chamber enclosed by the two vertical side bars, the top bar, and the bottom bar;
    a front panel in contact with the front face of the gel-frame, the front panel comprising an expanded upper portion, and
    a back panel in contact with the back face of the gel-frame, the back panel comprising a horizontal opening at the bottom of the back panel.

2. The gel-frame cassette of claim 1, further comprising a gel in the hollow chamber.

3. An automated bioprocessing device processing the gel-frame cassette of claim 2, comprising:
    an electrophoresis chamber comprising the gel-frame cassette of claim 2;
    a plurality of processing chambers; and
    a robotic arm configured to transport the gel-frame cassette or the gel-frame to a chamber of the plurality of processing chambers.

4. The automated bioprocessing device of claim 3, wherein the plurality of processing chambers comprises a separation chamber and an electroblotting chamber.

5. The automated bioprocessing device of claim 4, wherein the plurality of processing chambers further comprises a blocking chamber, a washing chamber, and an antibody-incubation chamber.

6. The automated bioprocessing device of claim 5, wherein the antibody-incubation chamber comprises two expandable pouches, wherein the expandable pouches are configured to accommodate a membrane-frame cassette in-between the two expandable pouches.

7. The automated bioprocessing device of claim 4, wherein the separation chamber comprises a wedge column configured to engage with the gel-frame cassette and remove the front panel and back panel from the gel-frame.

8. The automated bioprocessing device of claim 4, wherein the electroblotting chamber comprises two holding pads, and a membrane-frame cassette in-between the two holding pads.

9. The gel-frame cassette of claim 1, wherein the gel forms covalent bonds with at least part of contacting surfaces on the two vertical side bars, the top bar, and the bottom bar.

10. An automated bioprocessing device for Western blot, comprising:
    an electrophoresis chamber;
    a separation chamber;
    an electroblotting chamber; and
    a robotic arm configured to transport a gel-frame to any one of the electrophoresis chamber, the separation chamber, and the electroblotting chamber.

11. The automated bioprocessing device for Western blot of claim 10, further comprising a blocking chamber, a washing chamber, and an antibody-incubation chamber.

12. The automated bioprocessing device of claim 10, wherein the separation chamber comprises a wedge column.

* * * * *